(12) United States Patent
Luecke

(10) Patent No.: US 8,721,534 B1
(45) Date of Patent: May 13, 2014

(54) SPECULUM ASSEMBLY

(76) Inventor: James D. Luecke, Alpine, TX (US)

( * ) Notice: Subject to any disclaimer, the term of this patent is extended or adjusted under 35 U.S.C. 154(b) by 733 days.

(21) Appl. No.: 12/555,561

(22) Filed: Sep. 8, 2009

Related U.S. Application Data

(63) Continuation of application No. 11/055,734, filed on Feb. 11, 2005, now abandoned.

(51) Int. Cl.
*A61B 1/00* (2006.01)
*A61B 1/04* (2006.01)

(52) U.S. Cl.
USPC .......................... 600/184; 600/114; 600/115

(58) Field of Classification Search
USPC ......... 600/105, 114–116, 124, 125, 129, 184, 600/185, 197, 201, 203, 204, 207, 226, 600/186–196, 131, 104, 198–199, 220–223
See application file for complete search history.

(56) References Cited

U.S. PATENT DOCUMENTS

| 357,216 | A | * | 2/1887 | McCall | 600/184 |
|---|---|---|---|---|---|
| 2,548,602 | A | | 4/1951 | Greenburg | |
| 3,162,190 | A | * | 12/1964 | Del Gizzo | 600/123 |
| 3,831,587 | A | | 8/1974 | Boyd | |
| 3,866,599 | A | * | 2/1975 | Johnson | 600/342 |
| 4,284,081 | A | * | 8/1981 | Kasper et al. | 604/102.02 |
| 4,681,093 | A | * | 7/1987 | Ono et al. | 600/116 |
| 4,971,036 | A | * | 11/1990 | Collins | 600/202 |
| 5,545,122 | A | | 8/1996 | Spruill | |
| 5,645,519 | A | * | 7/1997 | Lee et al. | 600/114 |
| 5,716,329 | A | | 2/1998 | Dieter | |
| 5,730,725 | A | * | 3/1998 | Yoon | 604/101.05 |
| 5,795,289 | A | | 8/1998 | Wyttenbach | |
| 5,865,729 | A | | 2/1999 | Meehan et al. | |
| 6,306,081 | B1 | * | 10/2001 | Ishikawa et al. | 600/127 |
| 6,540,737 | B2 | | 4/2003 | Bacher et al. | |
| D474,275 | S | | 5/2003 | Tan | |
| 6,751,497 | B2 | | 6/2004 | Fraden | |
| 7,534,204 | B2 | * | 5/2009 | Starksen et al. | 600/116 |
| 7,604,633 | B2 | * | 10/2009 | Truckai et al. | 606/41 |
| 7,695,433 | B2 | * | 4/2010 | Simons | 600/186 |
| 2003/0199737 | A1 | | 10/2003 | Deslauriers et al. | |
| 2004/0199050 | A1 | * | 10/2004 | Richardson | 600/116 |
| 2006/0149136 | A1 | * | 7/2006 | Seto et al. | 600/204 |
| 2007/0287886 | A1 | * | 12/2007 | Saadat | 600/115 |
| 2009/0247969 | A1 | * | 10/2009 | Nishtala et al. | 604/328 |
| 2010/0081877 | A1 | * | 4/2010 | Vakharia | 600/121 |
| 2010/0280489 | A1 | * | 11/2010 | Nishtala et al. | 604/514 |

\* cited by examiner

*Primary Examiner* — Alireza Nia

(57) ABSTRACT

A speculum assembly includes a tubular shaped housing having a first open end, a second end open and a peripheral wall extending between the first and second ends. A tubular shaped bladder has an open forward end, an open rear end and a perimeter wall extending between the forward and rear ends. The rear end is attached to and is coextensive with the second end of the housing so that the bladder extends forward of the second end of the housing. The bladder is inflatable and flares outwardly from the rear end to the forward end when the bladder is inflate. A pump apparatus is fluidly coupled to the bladder. The pump apparatus is adapted for inflating the bladder so that the bladder extends outwardly away from the housing. A sleeve is mounted to the housing and covers the bladder when the bladder is deflated.

11 Claims, 6 Drawing Sheets

US 8,721,534 B1

SPECULUM ASSEMBLY

This application is a continuation in part of U.S. App. 11/055,734, filed on Feb. 11, 2005.

BACKGROUND OF THE DISCLOSURE

Field of the Invention

The present invention relates to speculum devices and more particularly pertains to a new speculum device for performing vaginal examinations.

SUMMARY OF THE INVENTION

The present invention meets the needs presented above by generally comprising a tubular shaped housing that has a first end, a second end and a peripheral wall extending between the first and second ends. Each of the first and second ends is open. A tubular shaped bladder has forward end, a rear end and a perimeter wall extending between the forward and rear ends. Each of the forward and rear ends is open. The bladder includes an inner wall and an outer wall. The housing is positioned in the bladder and is attached to the inner wall of the bladder. A pump apparatus is fluidly coupled to the bladder. The pump apparatus is adapted for inflating the bladder so that the bladder extends outwardly away from the housing.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
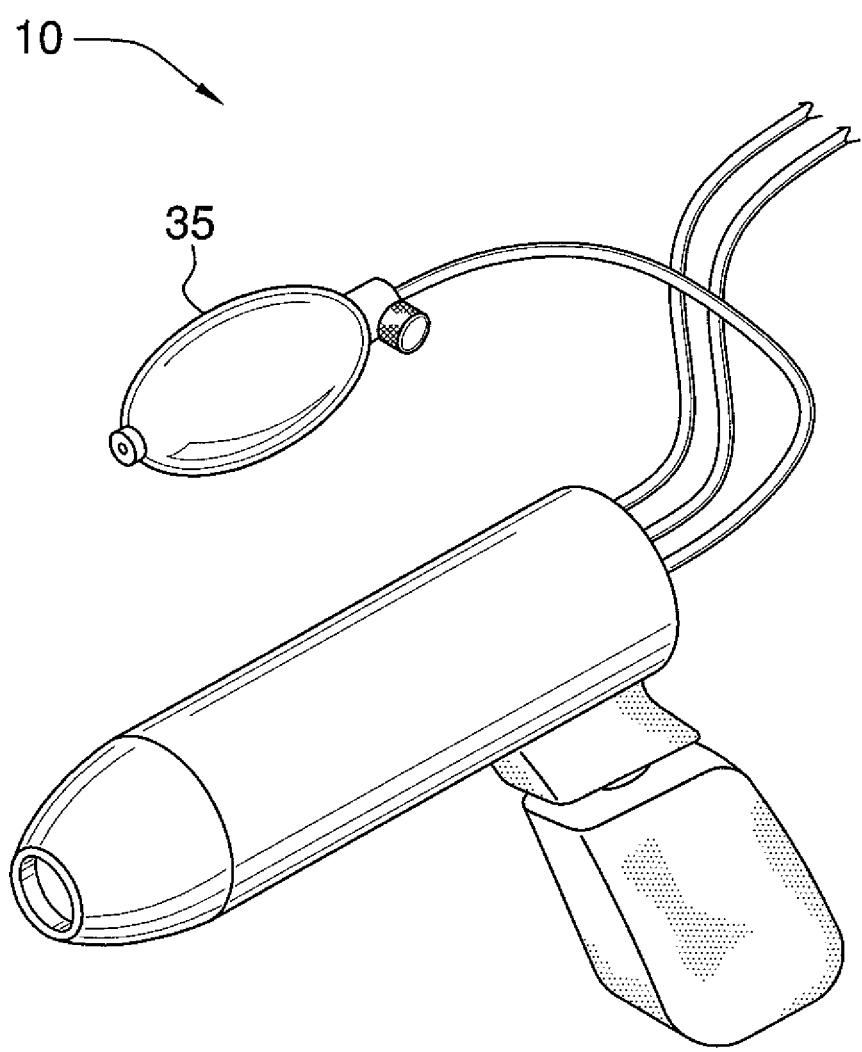
FIG. 1 is a perspective view of a speculum assembly according to the present invention.

With reference now to the drawings, and in particular to FIGS. 1 through 9 thereof, a new speculum device embodying the principles and concepts of the present invention and generally designated by the reference numeral 10 will be described.

As best illustrated in FIGS. 1 through 4, the speculum assembly 10 generally comprises a tubular shaped housing 12 that has a first end 14, a second end 16 and a peripheral wall 18 extending between the first 14 and second 16 ends. Each of the first 14 and second 16 ends is open.

A handle 20 is pivotally coupled to the peripheral wall 18. The handle 20 is positioned generally adjacent to the first end 14 of the housing 12. The handle 20 may be attached to the housing 12 with a pivot ball 22. Friction between the pivot ball 22 and the housing 12 retains the handle in a relative position with respect to the housing 12 unless urged into a different position.

Figure 3:
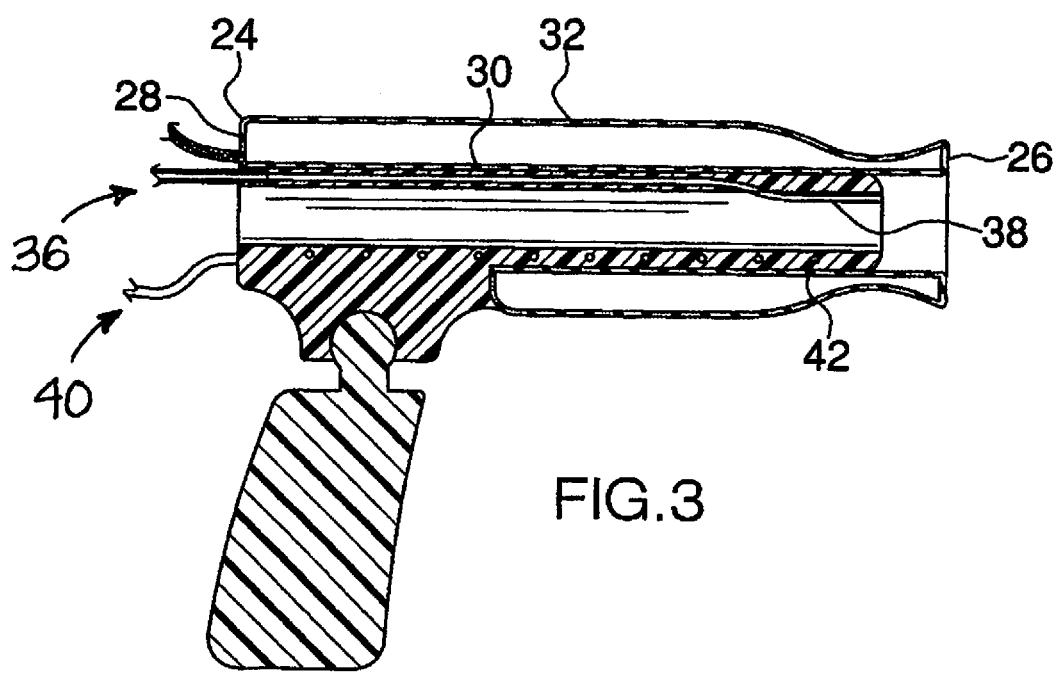
FIG. 3 is a cross-sectional view of the present invention.

A tubular shaped bladder 24 has forward end 26, a rear end 28. Each of the forward 26 and rear 28 ends is open. The bladder 24 includes an inner wall 30 and an outer wall 32. Together the inner 30 and outer 32 walls define a perimeter wall extending between the forward end 26 and the rear end 28. The housing 12 is positioned in the bladder 24 and is attached to the inner wall 30 of the bladder 24. The forward end 26 of the bladder 24 extends forward of the second end 16 of housing 12. The outer wall 32 adjacent to the forward end 26 preferably has a greater outer diameter with respect to remainder of the outer wall 32. This allows the forward end 26 to open radially outwardly when the bladder 24 is inflated to ensure adequate viewing through the housing 12 as shown in FIG. 3.

A pump apparatus 35 is fluidly coupled to the bladder 24. The pump apparatus 35 is adapted for inflating the bladder 24 such that the bladder 24 extends outwardly away from the housing 12. The pump apparatus 35 may either be manually actuated or electrically powered. The pump apparatus 35 may also be adapted for either pumping a fluid or air into the bladder 24.

Figure 2:
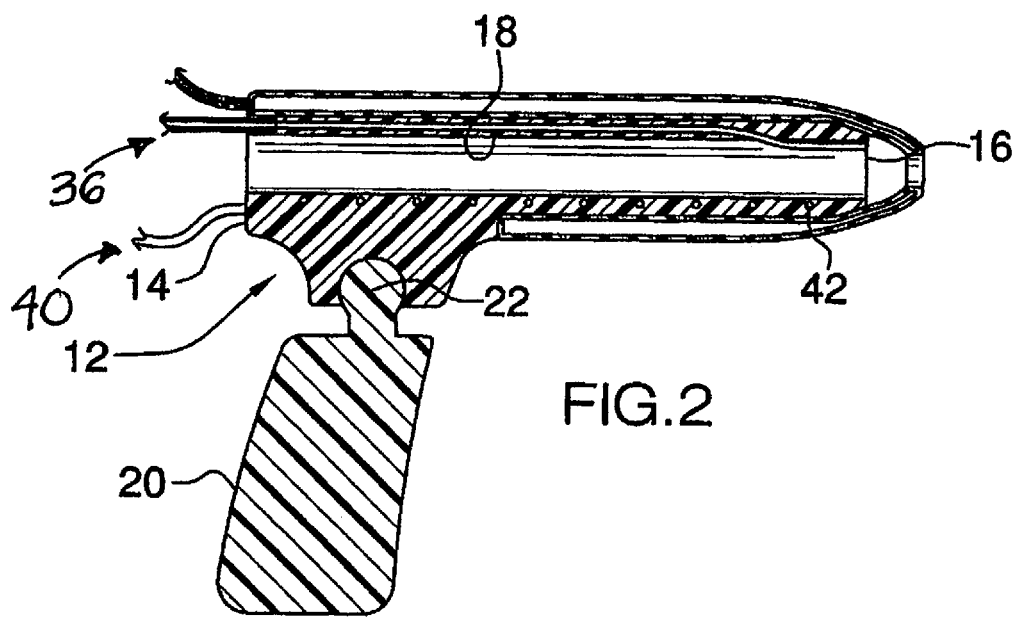
FIG. 2 is a cross-sectional view of the present invention.
Figure 4:
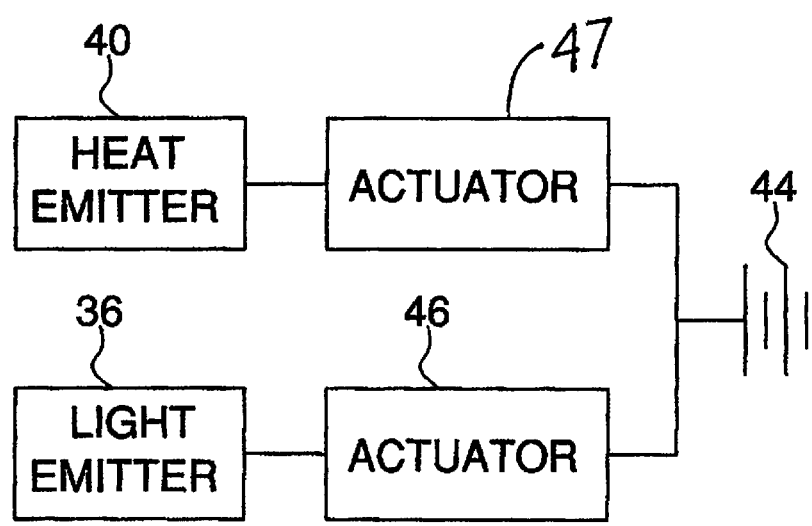
FIG. 4 is a schematic view of the present invention.
Figure 5:
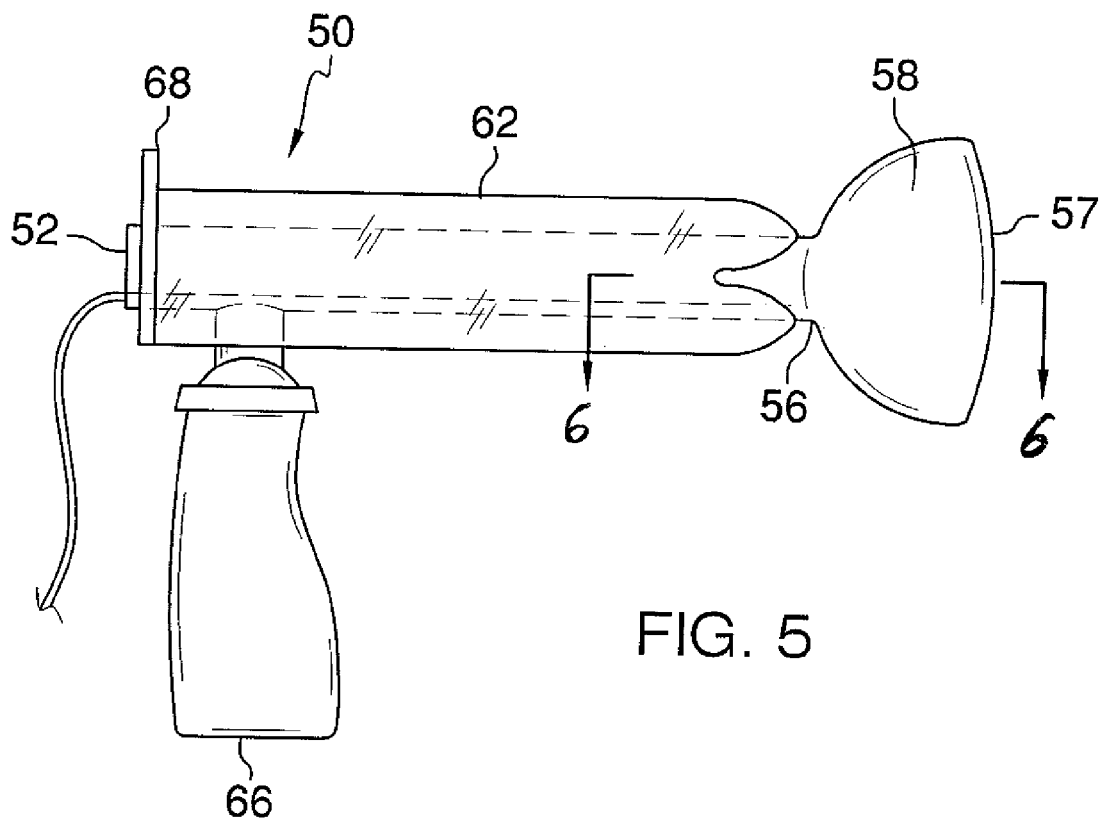
FIG. 5 is a side view of an embodiment of a speculum assembly according to the present invention.
Figure 6:
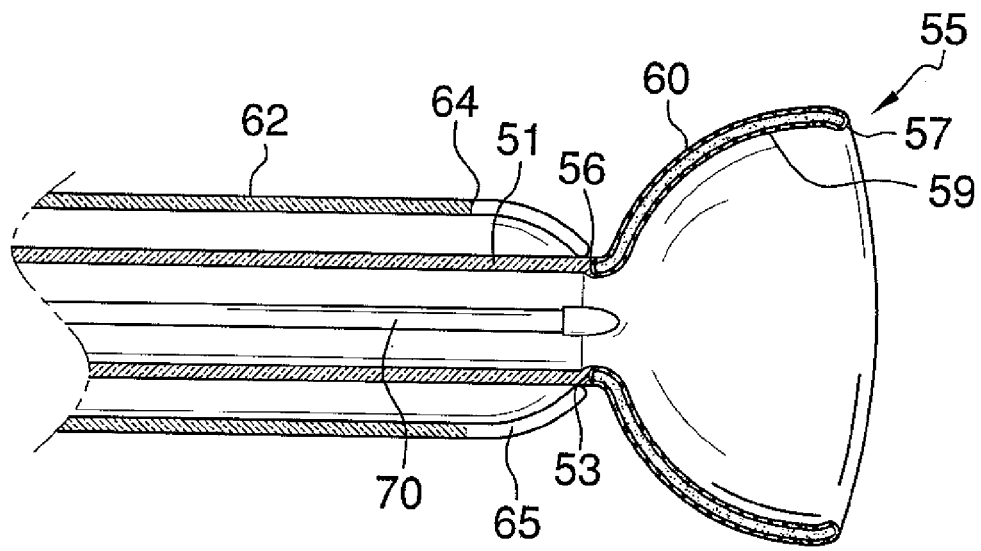
FIG. 6 is a cross-sectional view taken along line 6-6 of FIG. 5 of and embodiment the present invention.
Figure 7:
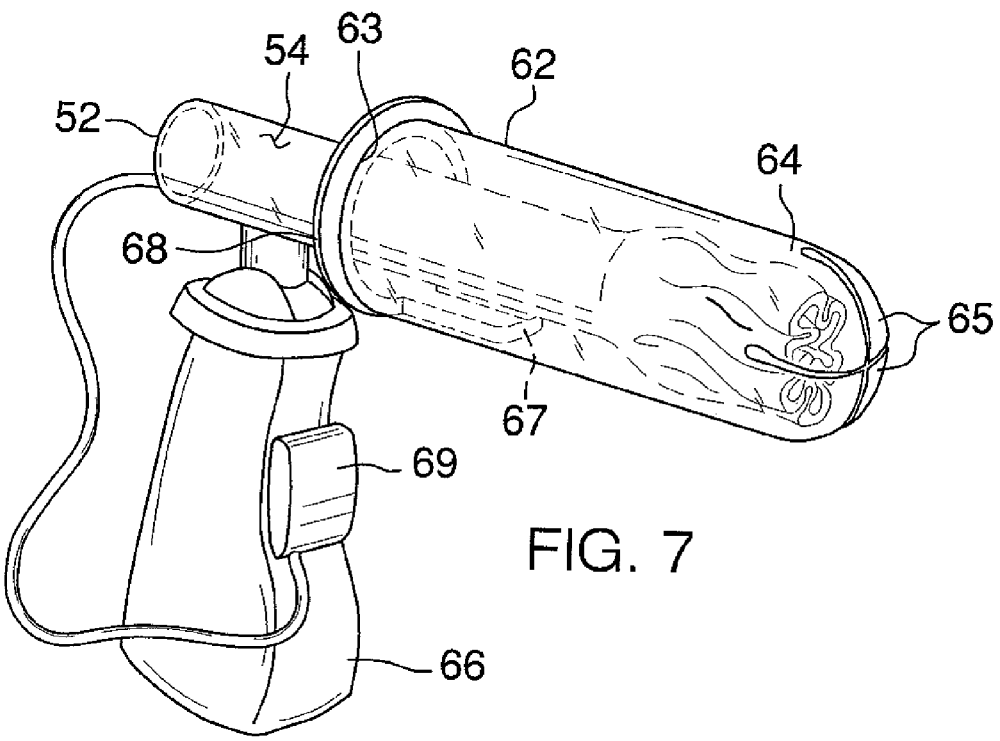
FIG. 7 is a front perspective view of an embodiment of the present invention.
Figure 8:
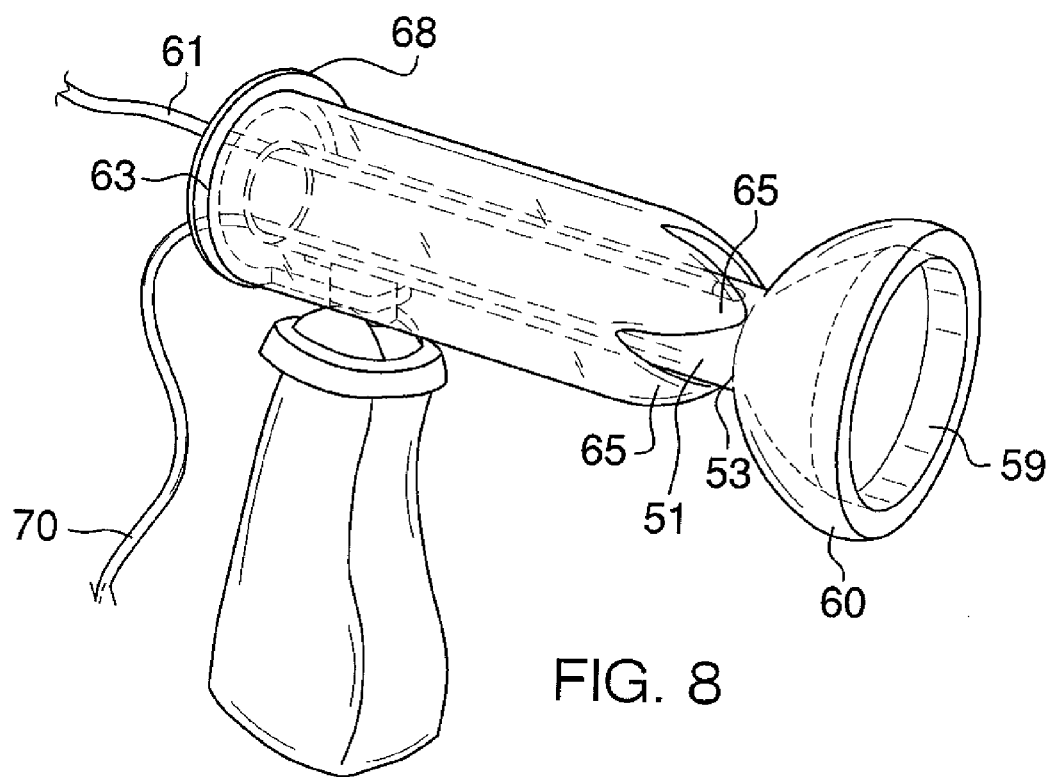
FIG. 8 is a front perspective view of an embodiment the present invention.
Figure 9:
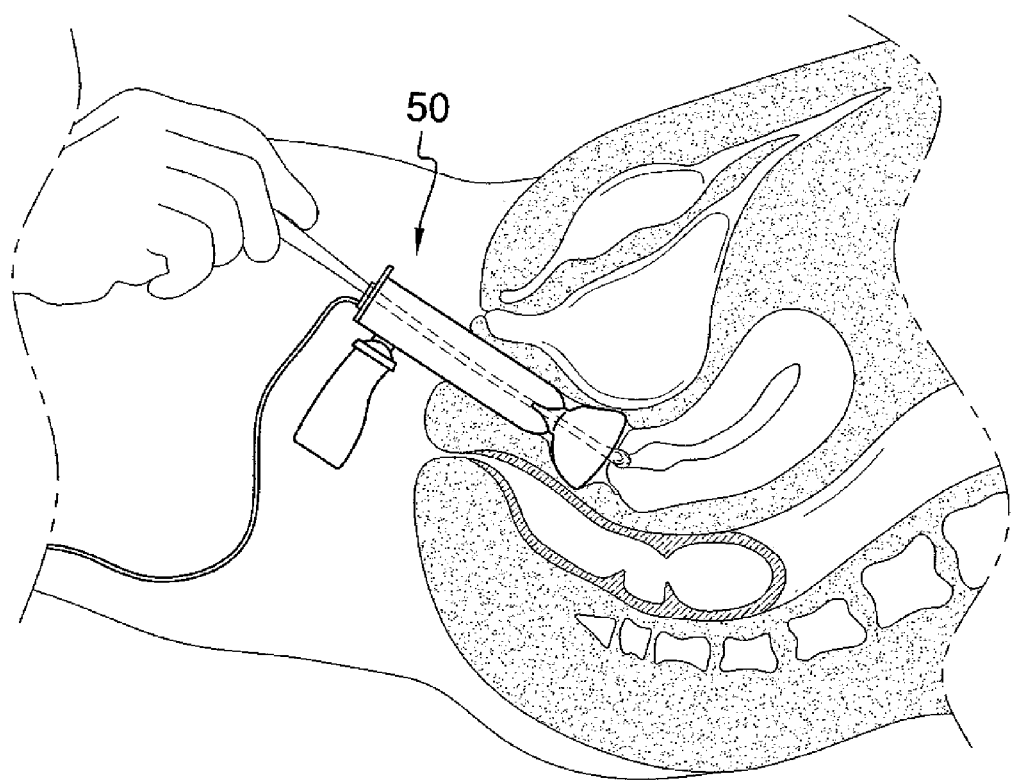
FIG. 9 is a side in-use view of an embodiment the present invention.

A light emitter 36 is mounted in the housing 12 and is directed toward the second end 16. As shown in FIGS. 2 and 3, the light emitter 36 may be specifically embodied by one or more fiber optic cables 38 extended along the housing 12. The fiber optic cables 38 may be positioned in the peripheral wall and extended outwardly of the second end 16. A heat emitter 40 is mounted in the peripheral wall 18 of the housing 12. The heat emitter 40 is adapted for heating the housing 12. In some embodiments, such as shown in cross section in FIGS. 2 and 3, the heat emitter 40 may be specifically embodied by heating coils 42 that are illustratively shown positioned in the peripheral wall 18. As shown in the schematic of FIG. 4, the heat emitter 40 and light emitter 36 are each respectively electrically coupled to a power supply 44 by the actuators 47, 46 for permitting selectively turning the heat emitter 40 and light emitter 36 on or off.

Another embodiment of the speculum assembly 50 is found in FIGS. 5-9. This embodiment 50 includes a tubular shaped housing 51 that has a first end 52, a second end 53 and a peripheral wall 54 extending between the first 52 and second 53 ends. Each of the first 52 and second 53 ends is open.

A tubular shaped bladder 55 has forward end 57, a rear end 56 and a perimeter wall 58 extending between the forward 57 and rear 56 ends. Each of the forward 57 and rear 56 ends is open. The bladder 55 includes an inner wall 59 and an outer wall 60. The rear end 56 is attached to and is coextensive with the second end 53 so that the bladder 55 extends forward of the second end 53 of the housing 51. The bladder 55 is inflatable. The bladder 55 flares outwardly from the rear end 56 to the forward end 57 when the bladder 55 is inflated. The bladder 55 forms a hemispherical shape having an increasing diameter from the rear end 56 to the forward end 57 when the bladder 55 is inflated. The outer wall 60 is convexly arcuate from the rear end 56 to the forward end 57 when the bladder 55 is inflated. The inner wall 59 may be concavely arcuate from the rear end 56 to the forward end 57 when the bladder 55 is inflated. As with the embodiment shown in FIGS. 1-4, the assembly 50 may include a light emitter 61 which is in the housing 51 and is directed toward the second end 53.

A pump apparatus 35 is fluidly coupled to the bladder 55 by a tube 70. The pump apparatus 35 is adapted for inflating the bladder 55 so that the bladder 55 extends outwardly away from the housing 51. The bladder 55 is inflated and expands when the pump apparatus 35 is actuated. The pump apparatus 35 may fill the bladder 55 with either a fluid or a gas. Though the pump apparatus 35 is shown as a hand pump in FIG. 1, it should be understood that the pump apparatus 35 may comprise either hand actuated or electrically powered pump assemblies.

A sleeve 62 is slidably mounted on the housing 51. The sleeve 62 has a proximal end 63 and a distal end 64 with respect to the first end 52 of the housing 51. The proximal end 63 is open and free of any closures. The distal end 64 is open has a plurality of flaps 65 attached thereto to selectively close the distal end 64. The flaps 65 comprise a resiliently flexible material and are positionable in a closed position extending beyond and covering the bladder 55 when the bladder 55 is in a deflated state or in an open position positioned between the bladder 55 and the first end 52 of the housing 51 when the bladder 55 is in an inflated state. The sleeve 62 is slidable toward the first end 52 of the housing 51 to release the bladder 55 from the sleeve 62 and the flaps 65 so that the bladder 55 may be inflated. The flaps 65 form a covering having an outer surface that is convexly arcuate when the flaps 65 are in the closed position.

A handle 66 is pivotally coupled to the housing 51. The handle 66 is positioned nearer to the first end 52 of the housing than the second end 53. The sleeve 62 has notch 67 therein extending inwardly of the proximal end 63. The notch 67 receives the handle 67 to allow the proximal end 63 to be slid toward the first end 52 of the housing 51.

In use, the housing 51, bladder 55 and sleeve 62 are inserted into a body orifice. The sleeve 62 is then slid back to expose the bladder 55 which is inflated with air or fluid. A flange 68 may be attached to the proximal end 63 to facilitate the sliding of the sleeve rearward. The air or fluid, as with the embodiment of FIG. 4, may be heated so that the bladder 55 is heated as well. A heat emitter may also be used to heat the housing 51 or the sleeve 62 as with the embodiment above. The housing 51 may be used for viewing into the orifice and the light emitter 61 turned on to illuminate the area being inspected. Another embodiment, shown in FIG. 7, may include handle mounted pump 69 fluidly coupled to the tube 70 to allow the user to better manipulate the inflation of the bladder 55.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A speculum assembly comprising:

a tubular shaped housing having an open first end, an open second end and a peripheral wall extending between said first and second ends, the peripheral wall of said housing defining a first portion of an inner passage extending from the open first end to the open second end of said housing;

a bladder having an open forward end, an open rear end and a perimeter wall extending between said forward and rear ends, the perimeter wall of said bladder including an inner wall and an outer wall, said rear end being attached to said second end of said housing so that said bladder extends forward of said second end of said housing, an opening of the rear end of said bladder being coextensive with an opening of the second end of said housing such that the perimeter wall of said bladder defines a second portion of the inner passage between the rear end and the forward end;

a pump apparatus being fluidly coupled to said bladder for inflating said bladder from a collapsed condition to an inflated condition such that said bladder extends outwardly away from said housing; and a sleeve being slidably mounted on said housing, said sleeve having a proximal end and a distal end with respect to said first end of said housing, said sleeve having a diameter tapering smaller at said distal end, said distal end being open having a plurality of flaps attached thereto to selectively close said distal end, said flaps comprising a resiliently flexible material and being positionable in a closed position extending beyond and covering said bladder when said bladder is in the collapsed condition and in an open position when said bladder is in said inflated condition, said sleeve being slidable toward said first end of said housing to release said bladder from said sleeve and said flaps so that said bladder may be inflated into said inflated condition;

wherein said bladder flares outwardly from said rear end to said forward end to form a substantially hemispherical shape having an increasing diameter from said rear end to said forward end, said outer wall being convexly arcuate from said rear end to said forward end and said inner wall being concavely arcuate from said rear end to said forward end when said bladder is in said inflated condition;

wherein said inner passage has a width at locations along a length of said inner passage, the width of said inner passage being either substantially uniform in dimension or increasing in dimension at all locations of the inner passage moving in a direction from the first end of the housing to the forward end of the bladder when the bladder is in said inflated condition; and a handle extending in a radial direction outwardly from an exterior location on said housing, wherein said sleeve has a notch formed therein, said notch extending inwardly from said proximal end toward said distal end for receiving said handle when said sleeve is moved rearwardly with respect to said housing to expose the forward end of said bladder, wherein the proximate end of said sleeve is continuous and unbroken about a circumference thereof.

2. The assembly according to claim 1, wherein the first portion of said inner passage of said housing has a substantially uniform width from the first end to the second end.

3. The assembly according to claim 2, wherein the substantially uniform width of the first portion of said inner passage forms a minimum width of said inner passage.

4. The assembly according to claim 2, wherein the second portion of said inner passage of said bladder has a width increasing from the rear end to the forward end when the bladder is in said inflated condition.

5. The assembly according to claim 1, said handle being pivotally 30 coupled to said housing toward said first end.

6. The assembly according to claim 1, further including a light emitter mounted on the perimeter wall of said housing to direct light into the inner passage without obstructing movement of a tool through the inner passage.

7. The assembly according to claim 1, wherein said sleeve has a substantially uniform exterior diameter from said proximal end toward said distal end, the flaps of said sleeve forming a covering having an outer surface being convexly arcuate when said flaps are in said closed position.

8. The assembly according to claim 1, wherein the proximal end of said sleeve being open and free of any closures to permit insertion of a tool into the through said inner passage.

9. The assembly according to claim 1, further including a heat emitter configured to heat said sleeve.

10. The assembly according to claim 1, further including a heat emitter configured to heat said housing.

11. A speculum assembly comprising:
  a tubular shaped housing having an open first end, an open second end and a peripheral wall extending between said first and second ends, the peripheral wall of said housing defining a first portion of an inner passage extending from the open first end to the open second end of said housing;
  a bladder having an open forward end, an open rear end and a perimeter wall extending between said forward and rear ends, the perimeter wall of said bladder including an inner wall and an outer wall, said rear end being attached to said second end of said housing so that said bladder extends forward of said second end of said housing, an opening of the rear end of said bladder being coextensive with an opening of the second end of said housing such that the perimeter wall of said bladder defines a second portion of the inner passage between the rear end and the forward end;
  a pump apparatus being fluidly coupled to said bladder for inflating said bladder from a collapsed condition to an inflated condition such that said bladder extends outwardly away from said housing; and
  a sleeve being slidably mounted on said housing, said sleeve having a proximal end and a distal end with respect to said first end of said housing, said sleeve having a diameter tapering smaller at said distal end, said distal end being open having a plurality of flaps attached thereto to selectively close said distal end, said flaps comprising a resiliently flexible material and being positionable in a closed position extending beyond and covering said bladder when said bladder is in the collapsed condition and in an open position when said bladder is in said inflated condition, said sleeve being slidable toward said first end of said housing to release said bladder from said sleeve and said flaps so that said bladder may be inflated into said inflated condition;
  wherein said bladder flares outwardly from said rear end to said forward end to form a substantially hemispherical shape having an increasing diameter from said rear end to said forward end, said outer wall being convexly arcuate from said rear end to said forward end and said inner wall being concavely arcuate from said rear end to said forward end when said bladder is in said inflated condition;
  wherein said inner passage has a width at locations along a length of said inner passage, the width of said inner passage being either substantially uniform in dimension or increasing in dimension at all locations of the inner passage moving in a direction from the first end of the housing to the forward end of the bladder when the bladder is in said inflated condition;
  wherein the first portion of said inner passage of said housing has a substantially uniform width from the first end to the second end, the substantially uniform width of the first portion of said inner passage forming a minimum width of said inner passage;
  wherein the second portion of said inner passage of said bladder has a width increasing from the rear end to the forward end when the bladder is in said inflated condition;
  a handle extending outwardly from an exterior location on said housing in a radial direction, said handle being pivotally coupled to said housing toward said first end;
  wherein said sleeve has a notch formed therein, said notch extending inwardly from said proximal end toward said distal end for receiving said handle when said sleeve is moved rearwardly with respect to said housing to expose the forward end of said bladder;
  a light emitter mounted on the perimeter wall of said housing to direct light into the inner passage without obstructing movement of a tool through the inner passage;
  a heat emitter configured to heat said sleeve;
  wherein said sleeve has a substantially uniform exterior diameter from said proximal end toward said distal end, the flaps of said sleeve forming a covering having an outer surface being convexly arcuate when said flaps are in said closed position;
  wherein the proximal end of said sleeve being open and free of any closures to permit insertion of a tool into the through said inner passage; and
  wherein the proximate end of said sleeve is continuous and unbroken about a circumference thereof.

* * * * *